(12) United States Patent
Appenzeller et al.

(10) Patent No.: US 8,579,945 B2
(45) Date of Patent: Nov. 12, 2013

(54) BONE STABILIZATION DEVICE

(75) Inventors: Andreas Appenzeller, Langendorf (CH); Daniel Fluri, Langendorf (CH)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

(21) Appl. No.: 13/197,539

(22) Filed: Aug. 3, 2011

(65) Prior Publication Data

US 2012/0203229 A1 Aug. 9, 2012

Related U.S. Application Data

(60) Provisional application No. 61/373,374, filed on Aug. 13, 2010.

(51) Int. Cl.
*A61B 17/80* (2006.01)
*A61B 17/88* (2006.01)

(52) U.S. Cl.
USPC ........................................................ 606/281

(58) Field of Classification Search
USPC .................. 606/60, 70, 71, 246–331
See application file for complete search history.

(56) References Cited

U.S. PATENT DOCUMENTS

| | | |
|---|---|---|
| 4,865,604 A | 9/1989 | Rogozinski |
| 4,988,350 A | 1/1991 | Herzberg |
| 5,006,120 A | 4/1991 | Garter |
| 5,059,193 A | 10/1991 | Kuslich |
| 6,190,408 B1 | 2/2001 | Melvin |
| 6,508,818 B2 * | 1/2003 | Steiner et al. ................ 606/71 |
| 6,780,185 B2 | 8/2004 | Frei et al. |
| 7,335,204 B2 | 2/2008 | Tornier |
| 2005/0165395 A1 | 7/2005 | Orbay et al. |
| 2005/0182405 A1 * | 8/2005 | Orbay et al. ................ 606/69 |
| 2008/0281326 A1 | 11/2008 | Watanabe et al. |
| 2010/0324602 A1 * | 12/2010 | Huebner et al. ............ 606/280 |

FOREIGN PATENT DOCUMENTS

| | | |
|---|---|---|
| CN | 2834438 | 11/2006 |
| CN | 2920191 | 7/2007 |
| DE | 19612276 | 10/1997 |
| EP | 1464295 | 10/2004 |
| FR | 2 785 519 | 5/2000 |
| UA | 27074 | 10/2007 |
| WO | 2005/044121 | 5/2005 |

* cited by examiner

*Primary Examiner* — Kevin T Truong
*Assistant Examiner* — Christopher Beccia
(74) *Attorney, Agent, or Firm* — Fay Kaplun & Marcin, LLP

(57) ABSTRACT

A bone plate for the stabilization of bones includes upper and lower surfaces extending along a central longitudinal axis. The lower surface is configured to contact a target portion of bone when in an operative configuration a through opening extending through the plate from the upper surface to the lower surface. The through opening is sized and shaped to receive a stabilization plate. The through opening has an elongated curved shape selected to conform to a cross-sectional shape of a proximal portion of the stabilization plate.

16 Claims, 7 Drawing Sheets

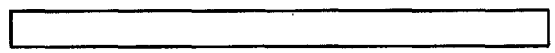
F I G. 6A
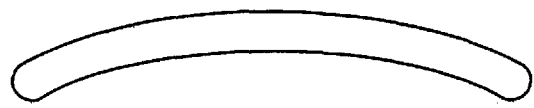
F I G. 6B
F I G. 6C
F I G. 6D
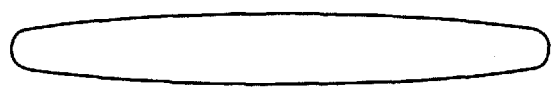
F I G. 6E
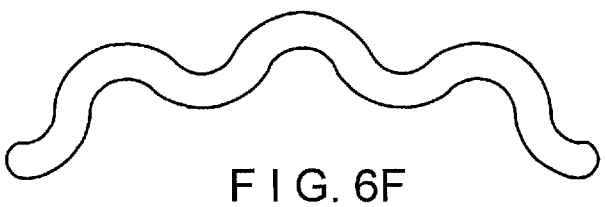
F I G. 6F

BONE STABILIZATION DEVICE

PRIORITY INFORMATION

The present application claims priority to U.S. Provisional Application Ser. No. 61/373,374 entitled "Bone Stabilization Device" filed on Aug. 13, 2010 to Andreas Appenzeller and Daniel Fluri. The entire contents of this application are incorporated herein by reference thereto.

FIELD OF THE INVENTION

The present invention generally relates to a device allowing fracture fixation in osteoporotic bone as well as to a method for stabilizing a bone by using said bone stabilization device.

BACKGROUND INFORMATION

A device for the fixation of bones is known from U.S. Pat. No. 7,335,204 to Tornier. This known device comprises a central plate with a plurality of smaller bone plates arranged along a periphery thereof, the smaller bone plates being configured to be bendable by a surgeon. Another device is known from EP Patent No. 1 464 295 and comprises a main plate and a cantilever plate attached thereto. In case of these known devices, the bone plates attached to the main plate are not insertable into bone but are fixed onto an outer surface thereof. One problem associated with the above described devices is that their application in osteoporotic bones does not provide sufficient stabilization. This results generally from the use of bone screws which are susceptible to losing bony purchase in osteoporotic bone, potentially leading to a collapse of the bone and/or screw sintering through a joint, as those skilled in the art will understand. It is therefore an object of the present invention to provide a device providing improved stabilization of osteoporotic bone.

SUMMARY OF THE INVENTION

The present invention relates to a system and method for improving a holding strength of a bone fixation device in a fractured, osteoporotic or otherwise damaged bone. The exemplary embodiment of the present invention comprises a bone plate with a longitudinal axis, an upper surface and a lower surface for facing a bone. The bone plate has a length L, a width B and a thickness D coinciding with a distance between the upper and lower surfaces. The bone plate defines a middle plane containing the longitudinal axis and a through opening extending between the upper and lower surfaces sized and shaped to receive a stabilization plate. The through opening has a shape corresponding to a curvature of the stabilization plate as will be described in greater detail hereafter.

The present invention also relates to a stabilization plate insertable into the through opening of the bone plate defining a longitudinal axis and including top and bottom sides. The stabilization plate is congruent with the through opening of the bone plate in that its shape and thickness are selected to cooperate with the cross-section and longitudinal curvature of the stabilization plate.

The present invention further relates to a bone stabilization device comprising the bone plate and at least one stabilization plate insertable in a through opening of the bone plate and rigidly fixable to the bone plate by fixation means.

The present invention further relates to a method for stabilizing bone by using this bone stabilization device.

For better understanding of the present invention, in particular of the shape of the through opening of the bone plate of the present invention as well as of the shape of the stabilization plate congruent to the shape of the through opening of the bone plate a detailed description is presented below.

The shape of the through opening of the bone plate essentially corresponds to a radial section of a body generated by rotating a planar closed curve about a rotation axis in the same plane as the closed curve. A most known geometrical body covered by this definition is the torus. The radial section is defined by two different planes through the rotation axis.

In geometry, a torus is a surface of revolution generated by revolving a circle in three dimensional space about an axis coplanar with the circle. In most contexts it is assumed that the axis does not touch the circle and in this case the surface has a ring shape and is called a ring torus or simply a torus if the ring shape is implicit. Other types of torii include the horn torus generated when the axis is tangent to the circle and the spindle torus generated when the axis is a chord of the circle.

According to the present invention the shape of the through opening is not restricted to torii generated by revolving a circle about an axis co-planar the circle but also includes forms generated by revolving other closed curves about axes co-planar therewith. Several possible embodiments of suitable closed curves are shown in FIG. 6.

The stabilization plate according to the present invention essentially has a shape congruent to the shape of the through opening of the bone plate. In other words the shape of the through opening allows rotation of the stabilization plate about the rotation axis of the body generated by rotating a planar closed curve, when introduced in the through opening, by minimal clearance of the stabilization plate in the through opening.

Consequently, it is to be understood that the stabilization plate has a shape corresponding to a radial section of a body generated by rotating a planar closed curve about a rotation axis in the same plane as the closed curve, whereby the planar closed curve, which defines the shape of the stabilization plate is similar to the planar closed curve defining the shape of the through opening of the bone plate. Exemplary embodiments of the closed curves are shown in FIG. 6.

The invention relates a bone plate for the stabilization of bones with a through opening essentially having a shape generated by rotating a planar closed curve about a rotation axis in the same plane as the closed curve and spaced from the closed curve whereby the rotation axis is not perpendicular to a middle plane being arranged at an equal distance between the upper and the lower surfaces of the bone plate.

In one of the exemplary embodiments of the present invention, the rotation axis is located in the middle plane or extends parallel thereto.

In a further exemplary embodiment the closed curve is at least partially concave.

In another exemplary embodiment the closed curve has a geometric center, whereby the minimal distance between the geometric center and the rotation axis is in the range between 20 mm and 50 mm.

In yet another exemplary embodiment the ratio of the thickness D to the width B is in the range between 0.1 and 0.15.

In still a further exemplary embodiment the cross-section of the through opening parallel to the middle plane is curved, so that the through opening is essentially kidney-shaped.

The present invention further comprises a stabilization plate insertable into the through opening of the bone plate, wherein the stabilization plate is congruent with the through opening of the bone plate.

In a further exemplary embodiment the stabilization plate comprises fixation means for rigid fixation of the stabilization plate in the through opening of the bone plate.

In another exemplary embodiment the bottom side of the stabilization plate is curved in the direction of its longitudinal axis, whereby the curvature has a radius R. The radius R of this curvature amounts to between 20 and 40 mm and allows better adaptation to the anatomy of the femur.

In again another exemplary embodiment the bottom side of the stabilization plate is curved transverse to its longitudinal axis, wherein the curvature has a radius r. The radius r of the curvature amounts to between 6 and 20 mm and improves support of the joint head.

In an additional exemplary embodiment the radius R of the curvature of the stabilization plate in the direction of its longitudinal axis is substantially identical to the radius r of the curvature of the stabilization plate transverse to its longitudinal axis. The spherical shape of the device improves its stability.

In a further exemplary embodiment, the stabilization plate has a front end which is self-cutting facilitating insertion into the bone.

In a further exemplary embodiment, the stabilization plate is provided with a number n of perforations allowing bone growth through the perforations as well as passing through of the anchoring elements (pins, K-wires, screws etc.) for improved anchoring.

In another exemplary embodiment the number n of perforations is between 50 and 100. This embodiment allows a more flexible placement of anchoring elements depending on the size/diameter of the anchoring elements.

In a further exemplary embodiment, at least part of the stabilization plate is configured as a grid allowing positioning of bone anchoring elements in an increased angular range.

In again another exemplary embodiment, the stabilization plate has a total area F and the perforations have a total area f, wherein the ratio F/f is in the range between 1.25 and 5.00 increasing the flexibility of the stabilization plate and the number of possibilities to implant bone anchoring elements therethrough and improving healing and blood circulation in the region of the fractured bone while reducing the risk of infection. This embodiment may also employ a bioresorbable plate and/or a growth promoter applied to either a bioresorbable or a non-resorbable plate.

In another exemplary embodiment the stabilization plate has a peripheral unperforated frame increasing the mechanical stability of the plate.

The present invention further comprises a bone stabilization device comprising a bone plate and at least one stabilization plate insertable in the through opening of the bone plate and rigidly fixable to the bone plate via the fixation means.

The fixation of the stabilization plate to the bone plate can be effected by positive locking (e.g. by means of a screw connecting the stabilization plate to the bone plate) or alternatively by non-positive locking such as a conical connection between a part of the stabilization plate and the through opening of the bone plate as well as by a combination of positive and non-positive locking. The fixation of the stabilization plate to the bone plate can be further effected by a snap-fit. The fixation of the stabilization plate into the through opening of the bone plate is preferably substantially free of clearance.

In another exemplary embodiment, the stabilization plate is fixable in the through opening of the bone plate.

In a further exemplary embodiment, the bone plate is provided with a number m>1 of through openings in combination with a number p>1 of bone stabilization plates. In this embodiment the radii R of the curvatures of each of the stabilization plates in the direction of its longitudinal axis is essentially identical to its radii r of curvature transverse to its longitudinal axis providing enhanced stability due to support of the stabilization plates by one another.

The number m of through openings of the bone plate is preferably 2, 3 or 4 and the number p of stabilization plates is 2, 3 or 4.

In another exemplary embodiment, the stabilization plates abut each other so that a higher stability of the bone stabilization device is achievable.

In a further exemplary embodiment the through openings in the bone plate are arranged in such a manner that stabilization plates inserted into the through openings form a structure which is essentially ellipsoid or spherical.

In yet a further exemplary embodiment the through openings have a minimal distance between each other which ranges from 5 to 30 mm.

In another exemplary embodiment the bone stabilization device comprises a support element insertable and rigidly fixable into a bore formed therein.

In an additional exemplary embodiment the bore is similar to the through opening and the support element is a support plate with a longitudinal axis formed similarly to the stabilization plate.

In a further exemplary embodiment the support plate is curved in the direction of its longitudinal axis and the curvature has a radius R1. The radius R1 of the curvature of the support plate is preferably between 20 and 50 mm.

In another exemplary embodiment the support plate is curved transverse to its longitudinal axis and the curvature has a radius r1. The radius r1 of the curvature of the support plate is preferably larger than 5 mm.

In a further exemplary embodiment the radii R and/or r of the curvatures of the stabilization plates and the radii R1 and/or r1 of the curvature of the support plate are different from each other.

In yet a further exemplary embodiment the support element is telescopic. This embodiment enhances the adaptability of the device to the anatomy.

In another exemplary embodiment the support element consists of a shape memory-alloy, such as Nitinol.

In a further exemplary embodiment the stabilization plate has a length l whereby the ratio of the length L of the bone plate to the length l of the stabilization plate is in the range 10 to 50.

The present invention further comprises a method for stabilizing bone comprising the steps of positioning a bone plate on a bone and fixing the bone plate thereto using fixation elements. A stabilization plate is inserted into and locked within a through opening of the plate.

BRIEF DESCRIPTION OF THE DRAWINGS

Several embodiments of the invention will be described in the following by way of example and with reference to the accompanying drawings in which:

FIG. 6A illustrates a first exemplary embodiment of the through opening extending though the bone plate according to the present invention;

FIG. 6B illustrates a second exemplary embodiment of the through opening extending through the bone plate according to the present invention;

FIG. 6C illustrates a third exemplary embodiment of the through opening extending through the bone plate according to the present invention;

FIG. 6D illustrates a fourth exemplary embodiment of the through opening extending through the bone plate according to the present invention;

FIG. 6E illustrates a fifth exemplary embodiment of the through opening extending through the bone plate according to the present invention;

FIG. 6F illustrates a sixth exemplary embodiment of the through opening extending through the bone plate according to the present invention;

DETAILED DESCRIPTION OF THE INVENTION

A bone plate according to the present invention relates, among other things, to the holding strength of a bone fixation device implanted in osteoporotic or otherwise weakened bone. An exemplary bone plate according to the present invention comprises a proximal portion shaped and sized for placement over an epiphysis of a bone and a distal portion shaped and sized for placement over a shaft of the bone. It is noted however that the exemplary bone plate according to the present invention may be placed over any portion of any bone as required to ensure a proper fixation without deviating from the spirit and scope of the present invention. For example, the exemplary bone plate of the present invention may be employed in the fixation of long bones, short bones, spinal bones and/or maxillofacial bones. The exemplary bone plate according to the present invention comprises a plurality of bone plate holes configured to receive bone fixation screws. The bone plate also comprises a plurality of slots extending over an increased width portion of the bone plate, the slots being configured and dimensioned to permit the insertion of segmental stabilization plates therethrough and into the bone to a predetermined depth, as will be discussed in greater detail later on. The exemplary stabilization plates according to the present invention may be formed with a curvature and size selected to increase and/or maximize a holding strength with the bone by increasing a contacting surface area with the bone, as those skilled in the art will understand. It is noted that although the present application is described with a predetermined number of stabilization plates, any number of stabilization plates may be employed without deviating from the spirit and scope of the present invention.

Figure 1:
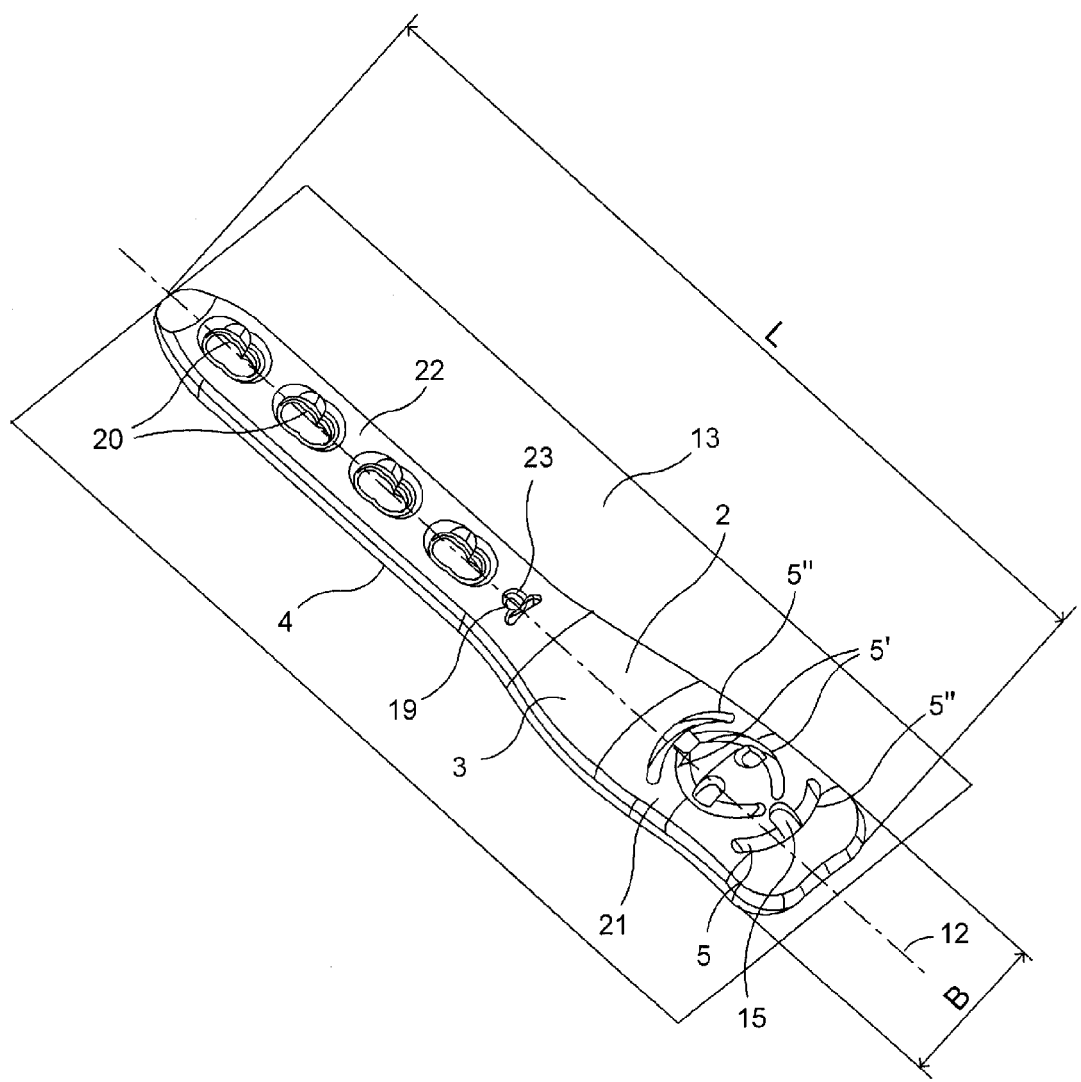
FIG. 1 illustrates a perspective view of an exemplary embodiment of the bone plate according to the present invention.

FIG. 1 illustrates an embodiment of a bone plate 2 with a central longitudinal axis 12, an upper surface 3 and a lower surface 4 which, in an operative configuration, faces a bone on which it is mounted. The bone plate 2 is seated in a middle plane 13 arranged at equal distances from the upper and lower surfaces 3, 4 and containing the central longitudinal axis 12. A proximal portion 21 of the bone plate 2 has a length L, a width B greater than a width of a distal portion 22 and a predetermined thickness between the upper surface 3 and the lower surface 4. The proximal portion 21 of the bone plate 2 comprises four through openings 5 extending from the upper surface 3 to the lower surface 4 each being configured to receive a stabilization plate 6 therethrough. Each of the through openings 5 has a shape corresponding to a radial cross-section of a respective one of the stabilization plates 6. The bone plate 2 and stabilization plates 6 according to the present invention may be formed of steel, titanium, PEEK, etc.

Each of the through openings 5 of the bone plate 2 may be formed with a different degree of curvature conforming to a degree of curvature of a corresponding one of the stabilization plates. For example, each of the through openings may have any of the cross-sectional shapes depicted in FIGS. 6A-6F and may be substantially planar, curved with one or more curvatures, elliptical, etc. It is noted that although the cross-sectional shapes depicted in FIGS. 6A-6F are substantially symmetric across a central longitudinal axis (not shown), any other asymmetric configuration may also be employed without deviating from the spirit and scope of the present invention. Furthermore, the through openings 5 may be disposed over the proximal portion 21 of the bone plate 2 in any configuration selected to conform to the requirements of a procedure being performed. In a first exemplary embodiment as shown in FIG. 1, a first pair 5' of through openings 5 are substantially symmetric with respect to and centered about the central longitudinal axis 12, angled so their concave surfaces face the central longitudinal axis 12. A second pair 5" of the through openings 5 is positioned proximally and distally, respectively, of the first pair 5' also centered relative to the central longitudinal axis 12. Longitudinal axes of the second pair 5" of the through openings 5 extend substantially perpendicularly to the central longitudinal axis 12. Furthermore, the second pair 5" of through openings 5 is configured with concave faces thereof directed toward the first pair 5' of through openings as shown in FIG. 1. It is noted that this embodiment is exemplary only and in no way limits the scope of the present invention, which may be provided with any number of through openings 5 extending therethrough in any desired configuration.

Each of the through openings 5 further comprises a central opening 15 extending through a central portion thereof, as shown in FIG. 1. The central opening 15 may be open to the through opening 5 and has an arced cross-sectional shape selected to conform to a shape of an abutment 14 provided on a proximal end of each of the stabilization plates 6, as will be described in greater detail later on. In one embodiment, the central opening 15 extends from the top surface 3 to the bottom surface 4 to permit a stabilization plate 6 to be secured directly to a target bone by inserting a bone screw through the abutment 14, as will be discussed in greater detail later on. In another embodiment, the central opening 15 may only extend only partly into the top surface 3 to a first predetermined depth selected so that a top surface of the abutment 14 rests flush against the top surface 3 in an operative configuration. A second opening (not shown) sized and configured to receive a shaft of a bone screw (not shown) may extend distally from the central opening 15 to the bottom surface 4 of the bone plate. In this embodiment, the bone screw (not shown) may be inserted through the abutment 14 received in the central opening 15 and extend through the second opening (not shown) and subsequently be received in the bone to lock the stabilization plate with respect to the bone and the bone plate 2, as those skilled in the art will understand.

The bone plate 2 further comprises a bore 19 extending through the distal portion 22 configured and dimensioned to receive a support plate (shown in FIGS. 4 and 5), as will be discussed in greater detail below. The bore 19 is further open to a central opening 23 formed substantially similarly to the central opening 15 and configured and dimensioned to received an abutment (not shown) located at a proximal end of the support plate 9. The bore 19 may have a cross-sectional shape that is one of planar and curved with any of a variety of curvatures. The distal portion 22 further comprises a plurality of screw holes 20 which may be any combination of a variety of types of screw holes such as, for example, variable angle screw holes, combination screw holes, etc., as those skilled in the art will understand.

Figure 2:
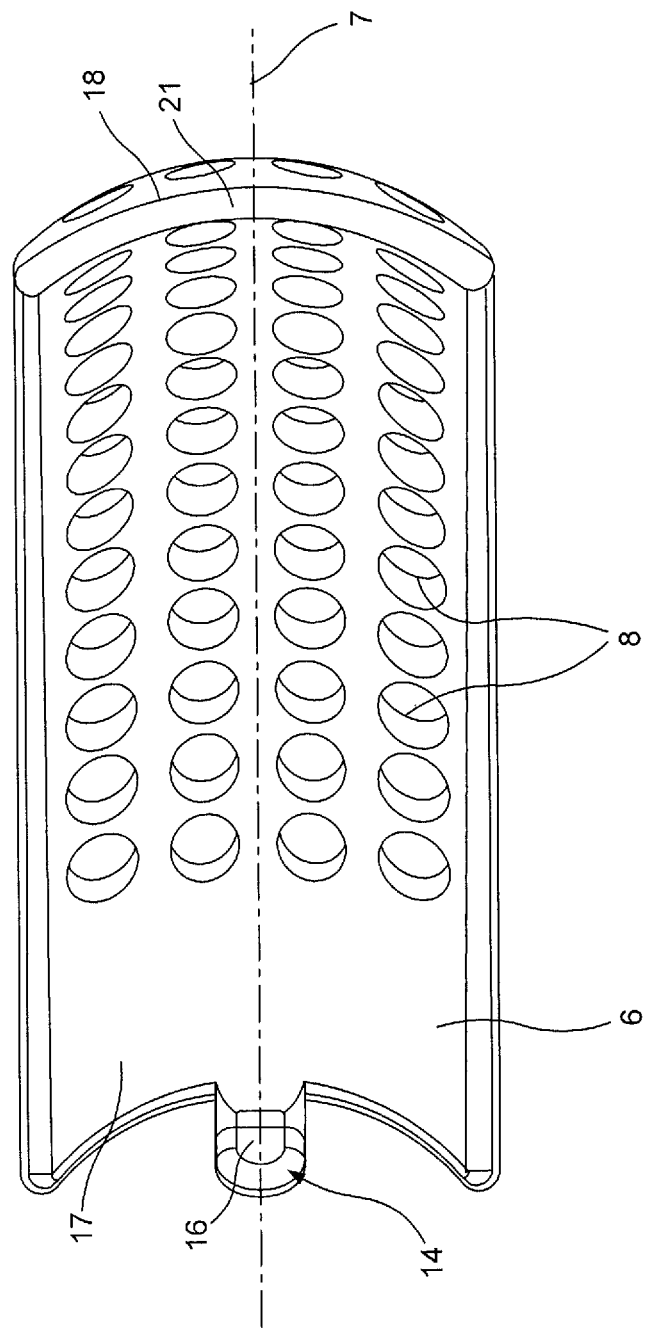
FIG. 2 illustrates a lateral view of an exemplary embodiment of the stabilization plate according to the present invention.

As shown in FIG. 2, a stabilization plate 6 according to a first embodiment of the present invention has a central longitudinal axis 7, a first surface 18 and a second surface 17. The abutment 14 is centered along the central longitudinal axis 17 and comprises an opening 16 extending therethrough, the opening 16 configured and dimensioned to receive a bone screw therethrough. The opening 16 may be threaded or non-threaded. In one embodiment, the abutment 14 is angled with respect to the stabilization plate 6 so that when the stabilization plate 6 is inserted through the through opening 5, the abutment 14 lies flush against the top surface 3 of the bone plate 2. In another embodiment, the abutment 14 may be configured to be bendable by a physician after insertion of the stabilization plate 6 through the opening 5 with the use of a proper bending tool, as those skilled in the art will understand.

The stabilization plates 6 are formed with a body having a first curvature extending along the central longitudinal axis 7 substantially symmetric with respect thereto, as shown in FIG. 2. As those skilled in the art will understand, the degree of curvature may be selected to conform to the requirements of a procedure being performed. The stabilization plates 6 may also have a second curvature extending substantially perpendicularly to the first curvature, as shown in FIGS. 2-5, the second curvature also being selected to conform to a procedure being performed. For example, the degree of the second curvature may be selected so that, once implanted into the bone, the stabilization plate 6 remains separated from an outer periphery of the bone by at least a predetermined distance along its length. The stabilization plate 6 further comprises a plurality of substantially circular perforations 8 extending therethrough and disposed thereover in any of a number of patterns. As those skilled in the art will understand, the perforations 8 promote bone ingrowth increasing a holding strength of the stabilization plate 6 in the bone. As those skilled in the art will further understand, the perforations 8 are separated from outer walls of the stabilization plate 6 by a predetermined distance to increase a rigidity thereof. A distal end 21 of the stabilization plate 6 may be configured to be self-cutting to facilitate the insertion of the stabilization plate 6 into the bone.

Figure 3:
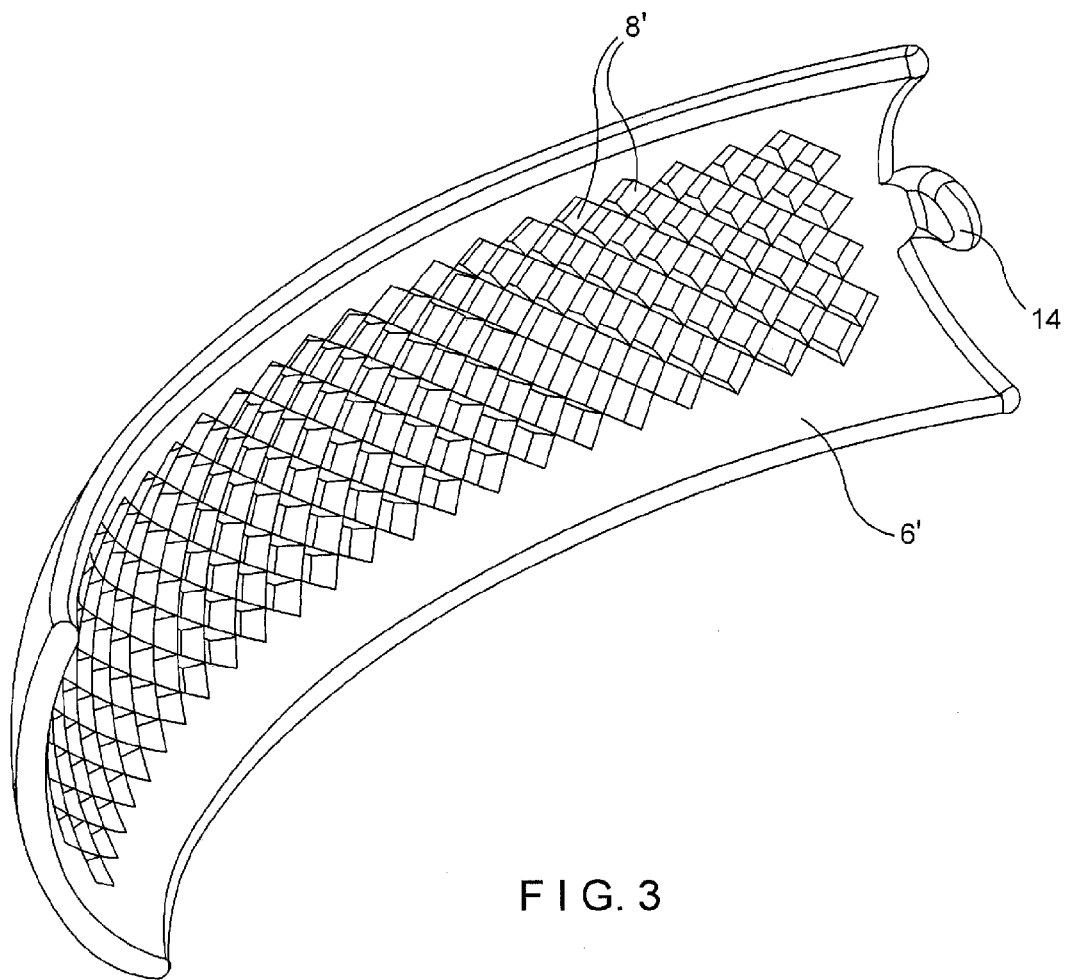
FIG. 3 illustrates a perspective view of another exemplary embodiment of the stabilization plate according to the present invention.

FIG. 3 illustrates another embodiment of a stabilization plate 6' according to the present invention. The stabilization plate 6' is formed substantially similarly to the stabilization plate 6 with the exception of the perforations 8 extending therethrough. Specifically, the perforations 8 are replaced by a mesh-like grid 8' having substantially rectangular openings extending through the stabilization plate 6'. It is further noted that the grid 8' may further be replaced by openings having any other cross-sectional shape without deviating from the spirit and scope of the present invention.

Figure 4:
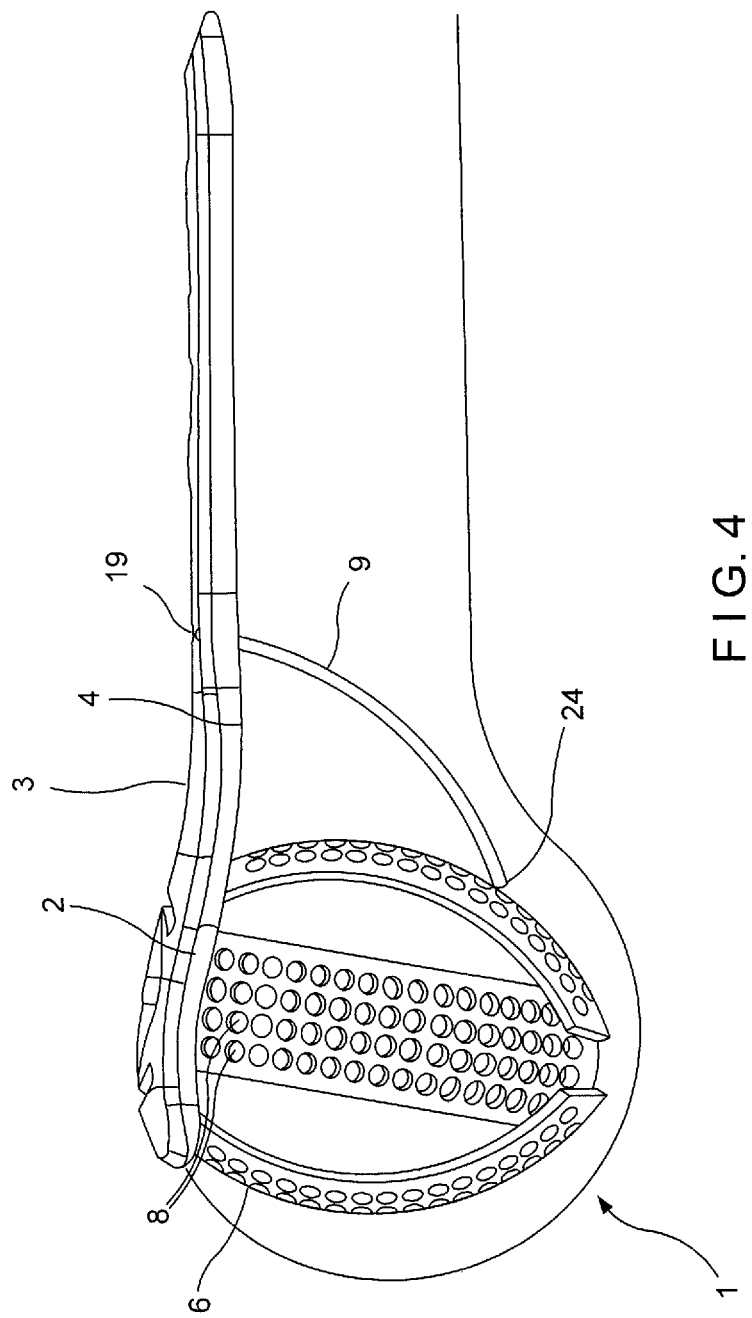
FIG. 4 illustrates a lateral view of an exemplary embodiment of the bone stabilization device according to the present invention.

FIG. 4 illustrates a perspective view of an embodiment of a bone stabilization device 1 comprising the bone plate 2 and several stabilization plates 6 inserted into the through openings 5 thereof. The stabilization plates 6 abut each other to form an essentially ellipsoid structure. The support element 9 is inserted through the bore 19 which, as shown in FIG. 4, has a cross-sectional shape corresponding to a cross-sectional shape of the support plate 9. The support plate 9 may be curved in substantially the same manner as the stabilization plate 6, as described in greater detail earlier. In one embodiment, the support element 9 may be curved so that a distal end 24 thereof abuts a distal most one of the stabilization plates 6 at a point located within the bone to form a joint construct. The support plate 9 of FIG. 4 may be formed with a uniform thickness. As shown in FIG. 4, the stabilization plates 6 are inserted into the bone in a manner selected to define a substantially spherical shape confirming to the substantially spherical shape of the epiphysis of the bone.

Figure 5:
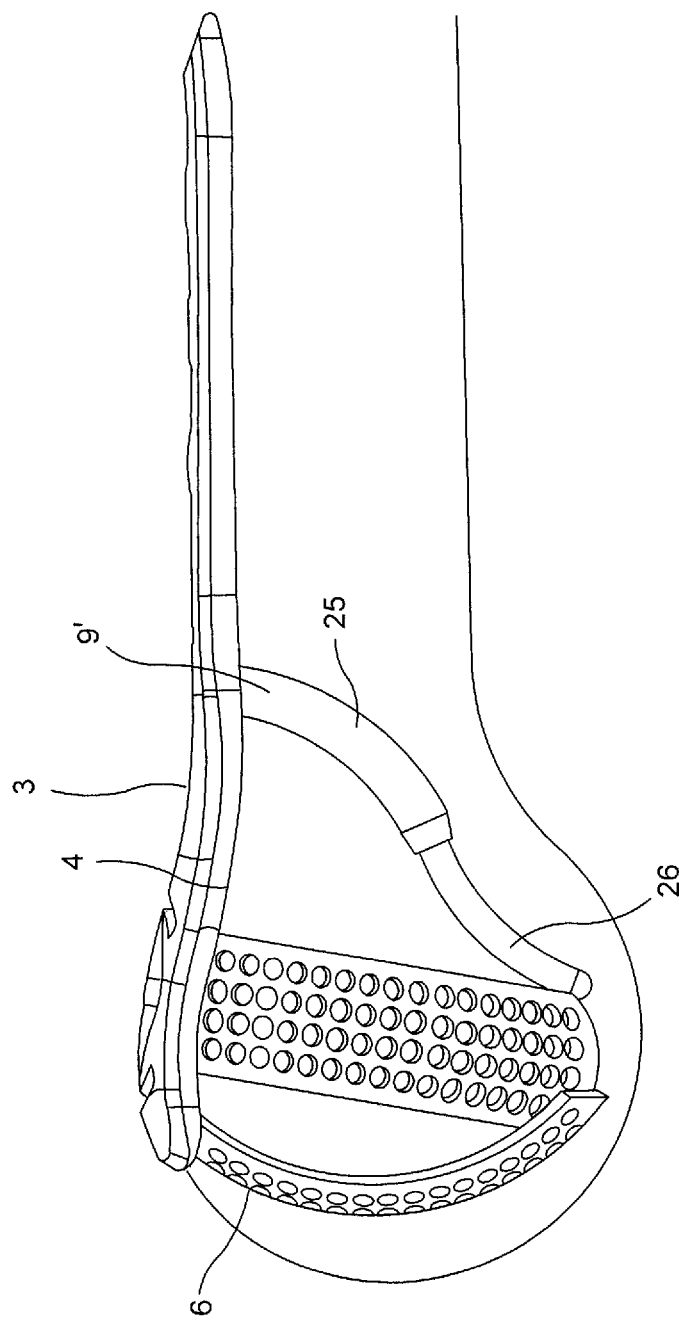
FIG. 5 illustrates a lateral view of another exemplary embodiment of the bone stabilization device according to the present invention.

FIG. 5 illustrates another embodiment of the bone stabilization device 1 according to the present invention. According to the embodiment of FIG. 5, a support element 9' has a form of a telescopic pin allowing an additional support of the construct composited by the stabilization plates 6. Specifically, the support element 9' comprises a proximal portion 25 having a first concave curvature and a first thickness. A distal portion 26 extends distally from the proximal portion 25 and has a second convex curvature and a second thickness smaller than the first thickness. The exemplary support element 9' may further be configured to contact any one of the stabilization plates 6 regardless of their position within the bone.

Figure 7:
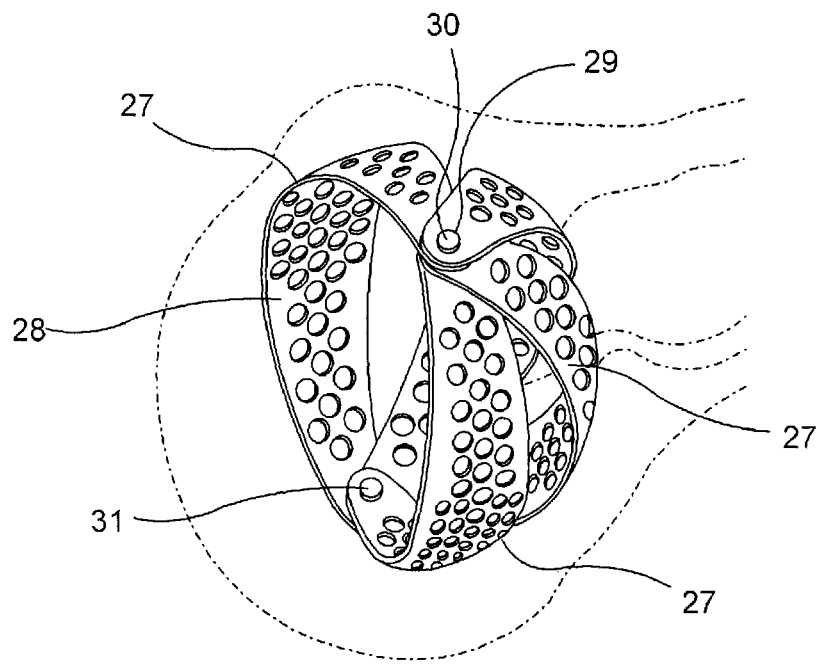
FIG. 7 depicts a perspective view of a stabilization device according to yet another exemplary embodiment according to the present invention.

FIG. 7 depicts another embodiment according to the present invention, wherein a bone fixation procedure comprises a plurality of stabilization plates 27 having a common proximal connection. Specifically, the stabilization plates 27 are formed substantially similarly to the stabilization plates 6 of FIG. 4. However, the stabilization plates 27 may be formed with a smooth transition from the plate body 28 to an opening 29 formed at a proximal end thereof to receive a bone fixation screw. The stabilization plates 27 may be employed with a bone plate (not shown) having a plurality of through holes 5 with a common central opening 15. This design will permit the individual insertion of each of the stabilization plates 27 into the bone so that, once fully inserted, respective openings 29 of the stabilization plates will be longitudinally aligned with one another. A single bone fixation screw 30 may then be inserted through the opening in the bone plate (not shown) and through each of the openings 29. A curvature and length of each of the stabilization plates 27 may be selected to permit distal ends 31 to contact one another at a point within the bone when implanted.

Figure 8:
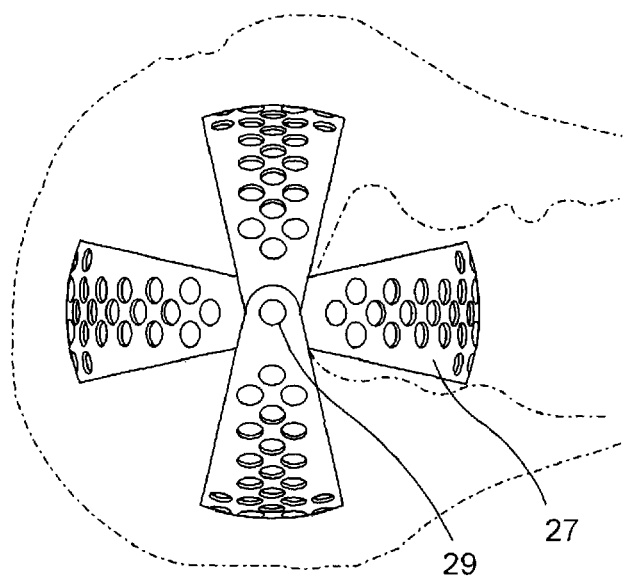
FIG. 8 depicts a perspective view of a stabilization device according to yet another exemplary embodiment according to the present invention.

FIG. 8 depicts another embodiment of the device described in FIG. 7. Specifically, the stabilization plates 27 of FIG. 8 are positioned to be equidistant from one another.

Although the invention and its advantages have been described in detail, it should be understood that various changes, substitutions, and alterations may be made herein without departing from the spirit and scope of the invention as defined by the appended claims. Moreover, the scope of the present application is not intended to be limited to the particular embodiments of the process, machine, manufacture, and composition of matter, means, methods and steps described in the specification. As those of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present invention.

It will be appreciated by those skilled in the art that various modifications and alterations of the invention can be made without departing from the broad scope of the appended claims. Some of these have been discussed above and others will be apparent to those skilled in the art.

What is claimed is:

1. A bone plate for stabilization of a bone, comprising:
 a first upper surface and a first lower surface extending along a central longitudinal axis, the first lower surface being configured to contact a target portion of bone when in an operative configuration; and
 a through opening extending through the bone plate from the first upper surface to the first lower surface, the through opening being sized and shaped to receive a stabilization plate, the through opening having an elongated curved shape selected to conform to a cross-sectional shape of a proximal portion of the stabilization plate.

2. The bone plate according to claim 1, wherein the through opening is symmetric across a central axis thereof.

3. The bone plate according to claim 1, wherein the through opening is formed as part of a three-dimensional shape formed by rotation of a concave closed curve about a rotation axis in the same plane as the closed curve.

4. The bone plate according to claim 3, wherein a distance between a geometric center of the closed curve and the rotation axis is range between 20 mm and 50 mm, the rotation axis being coplanar with the concave closed curve.

5. The bone plate according to claim 1, wherein a ratio of a thickness D between the first upper and first lower surfaces of the bone plate to a width B thereof substantially perpendicular to the central longitudinal axis of the bone plate is between 0.1 and 0.15.

6. The bone plate according to claim 1, wherein a cross-sectional shape of the through opening along an axis parallel to a middle plane housing the bone plate is one of non-circular and kidney shaped.

7. The bone plate according to claim 1, further comprising:
 a stabilization plate sized and shaped for insertion in the through opening of the bone plate, the stabilization plate extending along a stabilization plate longitudinal axis and including a second upper surface, a second lower surface and a fixation arrangement for rigidly fixing the stabilization plate in the through opening of the bone plate,
 wherein the second lower surface of the stabilization plate is curved in the direction of the stabilization plate longitudinal axis and wherein the curvature has a radius R,
 wherein the second lower surface is curved along an axis extending transverse to the stabilization plate longitudinal axis and wherein the curvature has a radius r, and
 wherein the radius R of the curvature of the stabilization plate in the direction of stabilization plate longitudinal axis and the radius r of the curvature of the stabilization plate transverse to the stabilization plate longitudinal axis are substantially identical.

8. The bone plate according to claim 7, wherein a front end of the stabilization plate is self-cutting.

9. The bone plate according to claim 7, wherein the stabilization plate includes a number n of perforations, the stabilization plate having a total area F and the perforations having a total area f, and wherein the ratio F/f is between 1.25 and 5.00 and wherein a peripheral frame of the stabilization plate is unperforated.

10. A system for stabilization of a bone, comprising:
 a bone plate including a first upper and a first lower surface extending along a central longitudinal axis, the first lower surface being configured to contact a target portion of bone in an operative configuration, the bone plate comprising a through opening extending therethrough from the first upper surface to the first lower surface wherein the through opening has an elongated curved shape; and
 a stabilization plate extending along a stabilization plate longitudinal axis configured and dimensioned for insertion into the through opening, a cross-sectional shape of the stabilization plate being congruent with a cross-sectional shape of the through opening, the stabilization plate including fixation arrangement rigidly fixing the stabilization plate to the bone plate.

11. The system according to claim 10, wherein the bone plate is provided with a number m>1 of the through openings, wherein the m through openings have a minimal distance between each other which ranges from 5 to 30 mm.

12. The system according to claim 10, wherein the system comprises p>1 stabilization plates, wherein a radius R of curvature of each stabilization plate in a direction parallel to the corresponding stabilization plate longitudinal axis is substantially identical to a radius r of curvature of the stabilization plate transverse to its stabilization plate longitudinal axis.

13. The system according to claim 11, wherein, in an operative configuration, the stabilization plates abut one another below an outer surface of the bone when the bone plate is implanted on an outer surface of the bone.

14. The system according to claim 10, further comprising:
 a support element configured and dimensioned for insertion and rigid fixation in a bore extending through the bone plate from the first upper surface to the first lower surface, the support element being a support plate extending along a support plate longitudinal axis configured and dimensioned for insertion into the bore, a cross-sectional shape of the support plate being congruent with a cross-sectional shape of the bore;
 wherein the support plate is curved in a direction of the support plate longitudinal axis and has a curvature with a radius R1 of between approximately 20 and 50 mm; and
 wherein the support plate is curved in a direction transverse to the support plate longitudinal axis and has a curvature with a radius r1 larger than 5 mm.

15. The system according to claim 14, wherein the support element is formed of a shape memory material.

16. The system according to claim 10, wherein the stabilization plate has a length l and wherein the ratio of a length L of the bone plate to the length l of the stabilization plate is between 10 and 50.

* * * * *